United States Patent
Coulthard et al.

(10) Patent No.: US 10,117,979 B2
(45) Date of Patent: Nov. 6, 2018

(54) SYSTEMS AND METHODS FOR ELECTRICALLY DETECTING THE PRESENCE OF EXUDATE IN DRESSINGS

(71) Applicant: KCI Licensing, Inc., San Antonio, TX (US)

(72) Inventors: Richard Daniel John Coulthard, Verwood (GB); Malcolm Thomson, San Antonio, TX (US); Rico Jaeger, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 234 days.

(21) Appl. No.: 14/318,204

(22) Filed: Jun. 27, 2014

(65) Prior Publication Data

US 2014/0336597 A1    Nov. 13, 2014

Related U.S. Application Data

(62) Division of application No. 13/183,245, filed on Jul. 14, 2011, now Pat. No. 8,795,257.

(Continued)

(51) Int. Cl.
*A61M 1/00* (2006.01)
*G08B 21/20* (2006.01)
(Continued)

(52) U.S. Cl.
CPC ..... *A61M 1/0092* (2014.02); *A61F 13/00055* (2013.01); *A61F 13/00068* (2013.01);
(Continued)

(58) Field of Classification Search
CPC . G08B 21/20; A61M 1/0025; A61F 13/00055
(Continued)

(56) References Cited

U.S. PATENT DOCUMENTS

| 116,562 A | * | 7/1871 | Collins | ............... A61N 1/0448 |
| | | | | 604/20 |
| 1,355,846 A | | 10/1920 | Rannells | |

(Continued)

FOREIGN PATENT DOCUMENTS

| AU | 550575 A1 | 3/1986 |
| AU | 745271 | 4/1999 |

(Continued)

OTHER PUBLICATIONS

N. A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

(Continued)

*Primary Examiner* — Paula L Craig (57) ABSTRACT

Systems and methods are provided for sensing fluid in a dressing on a patient and producing an electrical signal. In one instance, a galvanic cell is used as an electronic detection device. The galvanic cell is placed in the dressing and produces voltage when the dressing is substantially saturated. In one instance, the dressing is a reduced-pressure, absorbent dressing. Other systems, methods, and dressings are presented.

6 Claims, 5 Drawing Sheets

Related U.S. Application Data (60) Provisional application No. 61/418,730, filed on Dec. 1, 2010, provisional application No. 61/407,194, filed on Oct. 27, 2010, provisional application No. 61/365,614, filed on Jul. 19, 2010.

(51) Int. Cl.
*A61M 27/00* (2006.01)
*A61F 13/02* (2006.01)
*A61F 13/00* (2006.01)

(52) U.S. Cl.
CPC .......... *A61F 13/02* (2013.01); *A61F 13/0206* (2013.01); *A61F 13/0216* (2013.01); *A61M 1/009* (2014.02); *A61M 1/0031* (2013.01); *A61M 1/0088* (2013.01); *A61M 27/00* (2013.01); *G08B 21/20* (2013.01); *A61F 2013/0054* (2013.01); *A61F 2013/00174* (2013.01); *A61F 2013/00421* (2013.01); *A61F 2013/00536* (2013.01); *A61F 2013/00961* (2013.01); *A61M 1/0025* (2014.02); *A61M 2205/18* (2013.01); *A61M 2205/3317* (2013.01); *A61M 2205/3341* (2013.01); *A61M 2205/3344* (2013.01); *A61M 2205/3592* (2013.01); *A61M 2205/6081* (2013.01)

(58) Field of Classification Search
USPC .......................................................... 604/313
See application file for complete search history.

(56) References Cited

U.S. PATENT DOCUMENTS

| | | | |
|---|---|---|---|
| 2,547,758 A | 4/1951 | Keeling | |
| 2,632,443 A | 3/1953 | Lesher | |
| 2,644,024 A * | 6/1953 | Schumacher | H01M 12/06 429/406 |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,199,095 A * | 8/1965 | Ashida | A61F 13/42 128/886 |
| 3,367,332 A | 2/1968 | Groves | |
| 3,508,235 A * | 4/1970 | Baisden | A61F 5/48 128/886 |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,484,919 A * | 11/1984 | Sohn | A61F 5/4401 604/358 |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,266,928 A * | 11/1993 | Johnson | A61F 13/42 128/886 |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,793,294 A * | 8/1998 | Schepka | G01F 23/243 340/450 |
| 5,796,345 A * | 8/1998 | Leventis | A61F 13/42 340/604 |
| 5,959,535 A * | 9/1999 | Remsburg | A61F 13/42 128/886 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,580,013 B1 * | 6/2003 | Belloso | A61F 13/42 200/61.04 |
| 6,814,079 B2 | 11/2004 | Heaton et al. | |
| 8,579,872 B2 * | 11/2013 | Coulthard | A61F 13/02 604/317 |

(56) References Cited

U.S. PATENT DOCUMENTS

| | | | |
|---|---|---|---|
| 8,795,257 B2* | 8/2014 | Coulthard | A61F 13/02 604/313 |
| 9,265,665 B2* | 2/2016 | Robinson | A61M 1/0031 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0145525 A1* | 10/2002 | Friedman | A61B 5/0002 340/573.5 |
| 2004/0036484 A1* | 2/2004 | Tamai | A61F 13/42 324/663 |
| 2004/0230172 A1* | 11/2004 | Shapira | A61F 13/42 604/361 |
| 2005/0004550 A1* | 1/2005 | Sun | A61N 1/30 604/501 |
| 2005/0085751 A1* | 4/2005 | Daskal | A61N 1/0436 602/2 |
| 2005/0187580 A1* | 8/2005 | Skiba | A61N 1/303 607/2 |
| 2006/0079852 A1 | 4/2006 | Bubb et al. | |
| 2007/0078366 A1* | 4/2007 | Haggstrom | A61F 13/0203 602/53 |
| 2007/0265586 A1* | 11/2007 | Joshi | A61M 1/0031 604/313 |
| 2008/0058742 A1* | 3/2008 | Ales | A61F 13/42 604/361 |
| 2008/0064997 A1* | 3/2008 | Flick | A61F 13/00063 602/42 |
| 2008/0103462 A1* | 5/2008 | Wenzel | A61F 13/023 604/313 |
| 2008/0171957 A1* | 7/2008 | Connolly | A61B 5/0531 602/42 |
| 2009/0326492 A1* | 12/2009 | Hietpas | A61F 13/42 604/361 |
| 2010/0030167 A1* | 2/2010 | Thirstrup | A61F 5/445 604/318 |
| 2010/0130947 A1* | 5/2010 | Daly | A61M 1/0023 604/318 |
| 2010/0174250 A1* | 7/2010 | Hu | A61F 5/4401 604/319 |
| 2010/0318641 A1* | 12/2010 | Bullard | H04L 43/065 709/223 |
| 2011/0118655 A1* | 5/2011 | Fassih | A61N 1/044 604/20 |
| 2011/0230849 A1* | 9/2011 | Coulthard | A61M 1/0088 604/319 |
| 2011/0264062 A1* | 10/2011 | Locke | H01M 8/16 604/319 |
| 2012/0109083 A1* | 5/2012 | Coulthard | A61F 13/02 604/319 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| JP | H0719933 A | 1/1995 |
| SG | 71559 | 3/1999 |
| WO | 80/02182 A1 | 10/1980 |
| WO | 87/04626 A1 | 8/1987 |
| WO | 90/10424 A1 | 9/1990 |
| WO | 93/09727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2005099644 A2 | 10/2005 |
| WO | 2007130694 A2 | 11/2007 |
| WO | 2007133618 A2 | 11/2007 |
| WO | 2008095183 A2 | 8/2008 |
| WO | 2009093116 A1 | 7/2009 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

(56) References Cited

OTHER PUBLICATIONS

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Đukić, Ž. Maksimović, Đ. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians (Jul. 2007).

Japanese Notice of Rejection corresponding to JP2016-520759, dated May 30, 2017.

* cited by examiner

SYSTEMS AND METHODS FOR ELECTRICALLY DETECTING THE PRESENCE OF EXUDATE IN DRESSINGS

RELATED APPLICATION

This application is a division of U.S. patent application Ser. No. 13/183,245, entitled "Systems and Methods For Electrically Detecting The Presence of Exudate In Dressings," filed 14 Jul. 2011, which claims the benefit, under 35 USC § 119(e), of the filing of U.S. Provisional Patent Application Ser. No. 61/418,730, entitled "Systems and Methods for Electrically Detecting the Presence of Exudate in Dressings," filed 1 Dec. 2010, which is incorporated herein by reference for all purposes; U.S. Provisional Patent Application Ser. No. 61/407,194, entitled "System and Methods For Electrically Detecting The Presence of Exudate In Reduced-Pressure Dressings," filed 27 Oct. 2010, which is incorporated herein by reference for all purposes; and U.S. Provisional Patent Application Ser. No. 61/365,614, entitled "Inflatable Off-loading Wound Dressing Assemblies, Systems, and Methods," filed 19 Jul. 2010, each of which is incorporated herein by reference for all purposes.

FIELD

The present disclosure relates generally to medical treatment systems and, more particularly, but not by way of limitation, to systems and methods for electrically detecting the presence of exudates in dressings, such as absorbent, reduced-pressure dressings.

BACKGROUND

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad contains cells or pores that are capable of distributing reduced pressure to the tissue and channeling fluids that are drawn from the tissue. Reduced pressure may also be used to remove fluids and for other purposes.

SUMMARY

According to an illustrative embodiment, a dressing for receiving and retaining an ionic fluid includes an absorbent layer for placing in fluid communication with the tissue site and for receiving and retaining the ionic fluids. The absorbent layer has a first side and a second, patient-facing side. The dressing further includes a sealing member for covering the absorbent layer and a first galvanic cell associated with the absorbent layer. The first galvanic cell is configured to produce a voltage when the absorbent layer proximate to the first galvanic cell is substantially saturated with the ionic fluid.

According to another illustrative embodiment, a system for treating a tissue site on a patient with reduced pressure includes an absorbent layer for placing proximate to the tissue site, a sealing member for covering the dressing and a portion of the patient's epidermis to form a fluid seal, and a reduced-pressure source fluidly coupled to the absorbent layer for providing reduced pressure to the absorbent layer. The system further includes a galvanic cell associated with the absorbent layer. The galvanic cell is configured to produce a voltage when the absorbent layer proximate to the galvanic cell is substantially saturated with an ionic fluid. The system may also include a monitoring unit electrically coupled to the galvanic cell for receiving power or voltage from the galvanic cell.

According to another illustrative embodiment, a method for treating a tissue site includes providing a dressing. The dressing includes an absorbent layer for placing in fluid communication with the tissue site and for receiving and retaining ionic fluids. The absorbent layer has a first side and a second, patient-facing side. The dressing also includes a sealing member for covering the absorbent layer and includes a first galvanic cell associated with the absorbent layer. The first galvanic cell is configured to produce a voltage indicative of a full state when the absorbent layer proximate to the first galvanic cell is substantially saturated with the ionic fluid. The method also includes deploying the dressing proximate to the tissue site and electrically coupling the first galvanic cell to a monitoring unit. The monitoring unit is configured to produce a dressing-full signal when receiving a voltage indicative of a full state from the first galvanic cell. The method further includes providing reduced pressure to the dressing until the monitoring unit provides the dressing-full signal.

According to another illustrative embodiment, a dressing for treating a tissue site on a patient includes an absorbent layer for placing in fluid communication with the tissue site and for receiving and retaining ionic fluids. The absorbent layer has a first side and a second, patient-facing side. The dressing further includes a sealing member for covering the absorbent layer and a conductive loop fluidly coupled to the absorbent layer. The conductive loop has a first terminal, a second terminal, and at least one conductive gap. The conductive gap is sized and configured to be electrically bridged when covered with the ionic fluid.

According to another illustrative embodiment, a dressing for treating a tissue site on a patient includes an absorbent layer for placing in fluid communication with the tissue site and for receiving and retaining fluids. The absorbent layer has a first side and a second, patient-facing side. The dressing further includes a dye associated with the absorbent layer. The dye is operable to change colors when becoming wet. The dressing also includes a sealing member for covering the absorbent layer and an electrical optical sensor associated with the absorbent layer. The electrical optical sensor is configured to detect a change in color of the dye associated with the absorbent layer and to produce a signal when the change has been sensed.

According to another illustrative embodiment, a reduced-pressure treatment system includes a treatment manifold for placing in fluid communication with a tissue site and for receiving ionic fluids. The treatment manifold has a first side and a second, patient-facing side. The reduced-pressure treatment system further includes a sealing member for covering the treatment manifold, an absorbent layer disposed between the sealing member and the treatment manifold, an electronic detection device associated with the absorbent layer for producing an electrical signal indicative of at least a fully saturated state, and a wireless-communication-and-power subsystem. The wireless-communication-and-power subsystem includes an antenna, communication, and processing unit associated with the electronic detection device and a remote wireless communication and power unit configured to transmit power to the antenna, communication, and processing unit and to receive a signal therefrom.

Other features and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
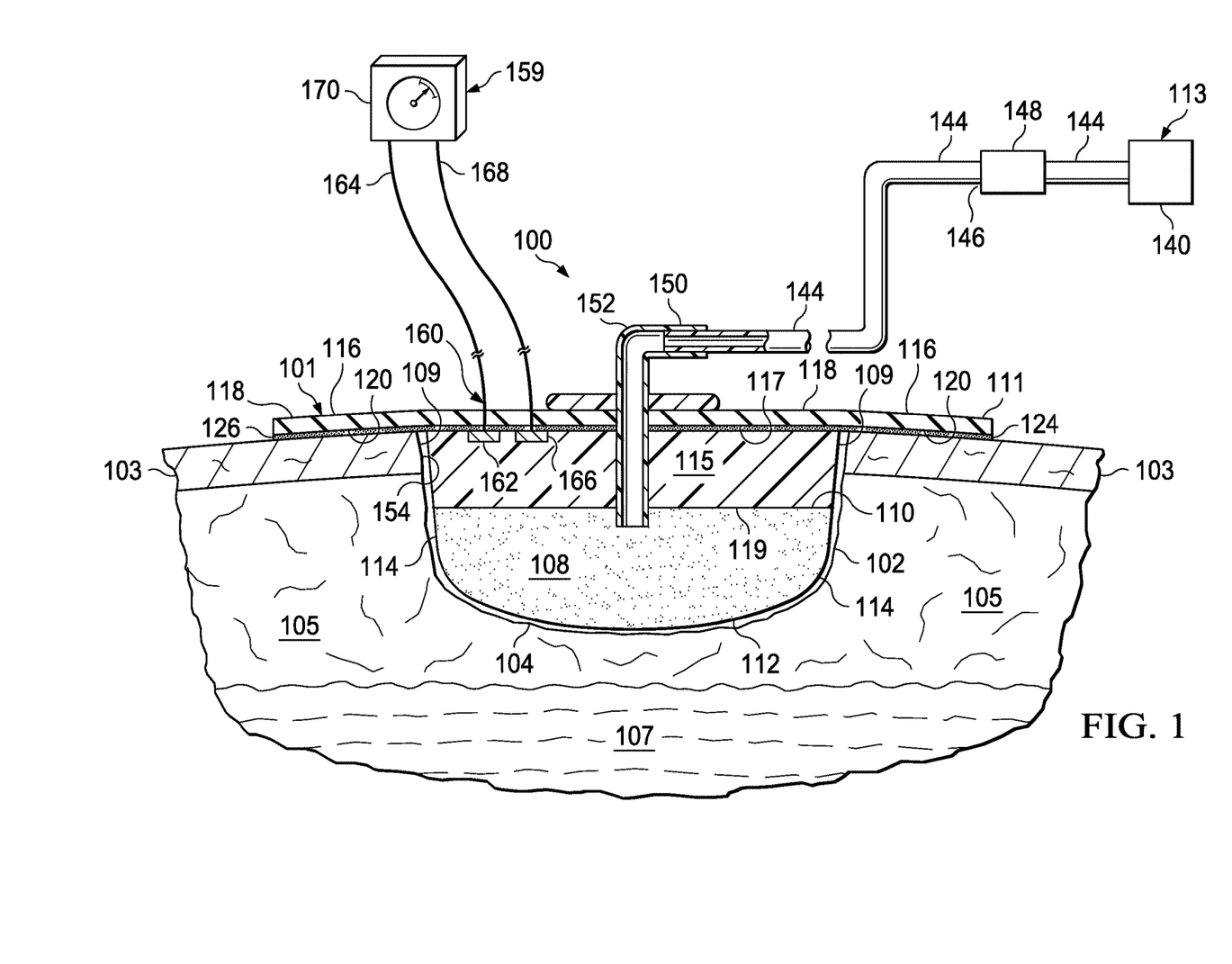
FIG. 1 is a schematic diagram with a portion shown in cross section of an illustrative embodiment of a reduced-pressure treatment system employing a galvanic cell to electrically sense the presence of exudates.

Referring now to the drawings and initially to FIG. 1, an illustrative embodiment of a reduced-pressure treatment system 100 and a dressing 101 for treating a tissue site 104, such as a wound 102, is presented. The wound 102 may be centered in a wound bed. The wound 102 may be through or involve epidermis 103, dermis 105, and subcutaneous tissue 107. The reduced-pressure treatment system 100 may also be used at other tissue sites. The tissue site 104 may be the bodily tissue of any human, animal, or other organism, including bone tissue, adipose tissue, muscle tissue, dermal tissue, vascular tissue, connective tissue, cartilage, tendons, ligaments, or any other tissue. Unless otherwise indicated, as used herein, "or" does not require mutual exclusivity.

The reduced-pressure treatment system 100 includes a treatment manifold 108 and an absorbent layer 115. Absorbent in the context of the absorbent layer or absorbent dressing means capable of at least temporarily retaining liquids. In addition, the reduced-pressure treatment system 100 may include a sealing member 111 and a reduced-pressure subsystem 113.

The treatment manifold 108 has a first side 110 and a second, patient-facing side 112. In one illustrative embodiment, the treatment manifold 108 is made from a porous and permeable foam or foam-like material and, more particularly, a reticulated, open-cell polyurethane or polyether foam that allows good permeability of wound fluids while under a reduced pressure. One such foam material that has been used is the VAC® GranuFoam®Dressing available from Kinetic Concepts, Inc. (KCI) of San Antonio, Tex. The manifold may be any substance or structure that is provided to assist in applying reduced pressure to, delivering fluids to, or removing fluids from the tissue site 104. A manifold typically includes a plurality of flow channels or pathways. The plurality of flow channels may be interconnected to improve distribution of fluids provided to and removed from the area of tissue around the manifold. Examples of treatment manifolds 108 may include, without limitation, devices that have structural elements arranged to form flow channels, cellular foam, such as open-cell foam, porous tissue collections, and liquids, gels, and foams that include or cure to include flow channels.

In one embodiment, the treatment manifold 108 may be constructed from bioresorbable materials that do not have to be removed from a patient's body following use of the dressing 101. Suitable bioresorbable materials may include, without limitation, a polymeric blend of polylactic acid (PLA) and polyglycolic acid (PGA). The polymeric blend may also include without limitation polycarbonates, polyfumarates, and capralactones. The treatment manifold 108 may further serve as a scaffold for new cell-growth, or a scaffold material may be used in conjunction with the treatment manifold 108 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

The absorbent layer 115 has a first side 117 and a second, patient-facing side 119. The absorbent layer 115 may be used alone or with the treatment manifold 108 or omitted from the reduced-pressure treatment system 100. The absorbent layer 115 may be coupled to the first side of the treatment manifold 108 or merely disposed proximate to the first side of the treatment manifold 108. The absorbent layer 115 may be formed with one or more layers including a wicking layer and a storage layer. For example, the absorbent layer 115 may be formed from superabsorbent polymers (SAP) of the type often referred to as "hydrogels," "super-absorbents," or "hydrocolloids." The absorbent layer 115 may also be formed from alginates or cellulose based materials.

The sealing member 111 covers the treatment manifold 108 and absorbent layer 115 and extends past a peripheral edge 114 of the treatment manifold 108 and absorbent layer 115 to form a sealing-member extension 116. The sealing-member extension 116 has a first side 118 and a second, patient-facing side 120. The sealing-member extension 116 may be sealed against the epidermis 103 or against a gasket or drape by a sealing apparatus 124, such as a pressure-sensitive adhesive 126. The sealing apparatus 124 may take numerous forms, such as an adhesive sealing tape, or drape tape or strip; double-sided drape tape; pressure-sensitive adhesive 126; paste; hydrocolloid; hydrogel; or other sealing means. If a drape tape is used, the tape may be formed of the same material as the sealing member 111 with a pre-applied, pressure-sensitive adhesive 126. The pressure-sensitive adhesive 126 may be applied on the second, patient-facing side 120 of the sealing-member extension 116. The pressure-sensitive adhesive 126 provides a substantial fluid seal between the sealing member 111 and the epidermis 103, which, as used herein, may also deemed to include a gasket or drape against the epidermis 103. Before the sealing member 111 is secured to the epidermis 103, removable strips (not shown) covering the pressure-sensitive adhesive 126 may be removed. A fluid seal is adequate to maintain reduced pressure at a desired site given the particular reduced-pressure source or subsystem involved.

The sealing member 111 may be an elastomeric material or any material or substance that provides a fluid seal. Elastomeric means having the properties of an elastomer and generally refers to a polymeric material that has rubber-like properties. More specifically, most elastomers have an ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Further still, the sealing member 111 may include a silicone drape, 3M Tegaderm® drape, PU drape such as one available from Avery Dennison Corporation of Pasadena, Calif.

The reduced-pressure subsystem 113 includes any device or devices that supply reduced pressure to the tissue site 104, and typically, to the treatment manifold 108. The reduced-pressure subsystem 113 typically includes a reduced-pressure source 140, which may take many different forms. The reduced-pressure source 140 provides reduced pressure as a part of the reduced-pressure treatment system 100. Reduced pressure generally refers to a pressure less than the ambient pressure at a tissue site 104 that is being subjected to treatment. In most cases, this reduced pressure will be less than the atmospheric pressure at which the patient is located. Alternatively, the reduced pressure may be less than a hydrostatic pressure at a tissue site. Unless otherwise indicated, values of pressure stated herein are gauge pressures.

The reduced pressure delivered may be constant or varied (patterned or random) and may be delivered continuously or intermittently. Consistent with the use herein, an increase in reduced pressure or vacuum pressure typically refers to a relative reduction in absolute pressure.

A portion 146 of the reduced-pressure delivery conduit 144 may have one or more devices, such as a representative device 148. The device 148 may be, for example, a fluid reservoir to hold exudates and other fluids removed, a pressure-feedback device, a volume detection system, a blood detection system, an infection detection system, a flow monitoring system, or a temperature monitoring system. Multiple devices 148 may be included. Some of these devices 148 may be integrated with the reduced-pressure source 140.

The reduced-pressure source 140 may be any device for supplying a reduced pressure, such as a portable therapy unit, a stationary therapy unit, micropump, or other device. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa).

The reduced pressure developed by reduced-pressure source 140 is delivered through the reduced-pressure delivery conduit 144 to a reduced-pressure interface 150, which may include an elbow port 152. In one illustrative embodiment, the reduced-pressure interface 150 is a T.R.A.C.® Pad or Sensa T.R.A.C.® Pad available from KCI of San Antonio, Tex. The reduced-pressure interface 150 allows the reduced pressure to be delivered through the sealing member 111 to the treatment manifold 108, as well as to a sealed treatment space 154, in which the treatment manifold 108 is located. In this illustrative embodiment, the reduced-pressure interface 150 extends through the sealing member 111 and into the treatment manifold 108. In another illustrative embodiment, the reduced-pressure interface 150 delivers reduced pressure to the absorbent layer 115 and the absorbent layer 115 delivers the reduced pressure to the treatment manifold 108.

While a reduced-pressure interface 150 is shown in FIG. 1, it should be understood that the reduced-pressure treatment system 100 may be used without the reduced-pressure interface 150. For example, the reduced-pressure delivery conduit 144 may be disposed through an aperture in the sealing member 111 and into the absorbent layer 115. Alternatively, the reduced-pressure delivery conduit 144 may be placed under an edge of the sealing member 111 and into the absorbent 115 or the treatment manifold 108 and sealed. The reduced-pressure delivery conduit 144 may be sealed using, for example, a drape tape.

An electronic detection device 159 is used to determine when the absorbent layer 115 is at least substantially saturated. The absorbent layer 115 becomes substantially saturated when the absorbent layer 115 fills with a liquid or when the area near the electronic detection device 159 becomes wet from the position of the dressing. As an example of the electronic detection device 159, one or more galvanic cells, e.g., a first galvanic cell 160, may be associated with the absorbent layer 115 to assess the presence of an ionic fluid, e.g., exudate. The electronic detection device 159 is typically placed such that the electronic device 159 contacts the absorbent layer 115 at locations where liquid will gather as the absorbent layer 115 becomes saturated. The electronic detection device 159 may be located on the sealing member 111 or within the absorbent material of the absorbent layer 115. Where the electronic detection devices 159 are mounted on the sealing member 111, electrical contact can be made to the sensing hardware directly through apertures in the sealing member 111. When wires or the direct contact method is used, the wires or components extend through the sealing member 111. The wires or components are sealed with respect to the sealing member 111 where the wires or components pass through the sealing member 111 in order to maintain the integrity of the reduced pressure, i.e., to maintain a fluid seal.

The first galvanic cell 160 produces a small current when the absorbent layer 115 proximate to the first galvanic cell 160 is substantially saturated with the ionic fluid. Typically, the first galvanic cell 160 will be located at a location that will experience the ionic fluid last as the absorbent layer 115 receives fluids from the tissue site 104 or the treatment manifold 108, and thereby functions as a full indicator for the absorbent layer 115. In other words, when the absorbent layer 115 is saturated, the first galvanic cell 16 produces a signal indicative of the same.

The first galvanic cell 160 includes a first electrode 162 that is electrically coupled to a first electrical lead 164. The first galvanic cell 160 also includes a second electrode 166 that is spaced from the first electrode 162 and that is electrically coupled to a second electrical lead 168. The first electrode 162 and second electrode 166 are formed from different conducting materials suitable for use with a galvanic cell. For example, in one illustrative embodiment, the first electrode 162 is copper (Cu) and the second electrode 166 is tin (Sn). In another illustrative embodiment, the first electrode 162 is copper (Cu) and the second electrode 166 is zinc (Zn). In another illustrative embodiment, the first electrode 162 is nickel (Ni) and the second electrode 166 is aluminum (Al). Almost any combination of materials on an electrochemical potential chart may be used, e.g., any combination of two of the following: F, Cl, Pt, Hg, Ag, I, Cu, Pb, Ni, Fe, Zn, Al, Na, Ca, K, or Li. The selected combination of metals should be dissimilar. Alloys will impact the exact voltage measured. Some combinations of metals on the list of metals would not be practical if elementally pure, such as Li, K and others.

Figure 2:
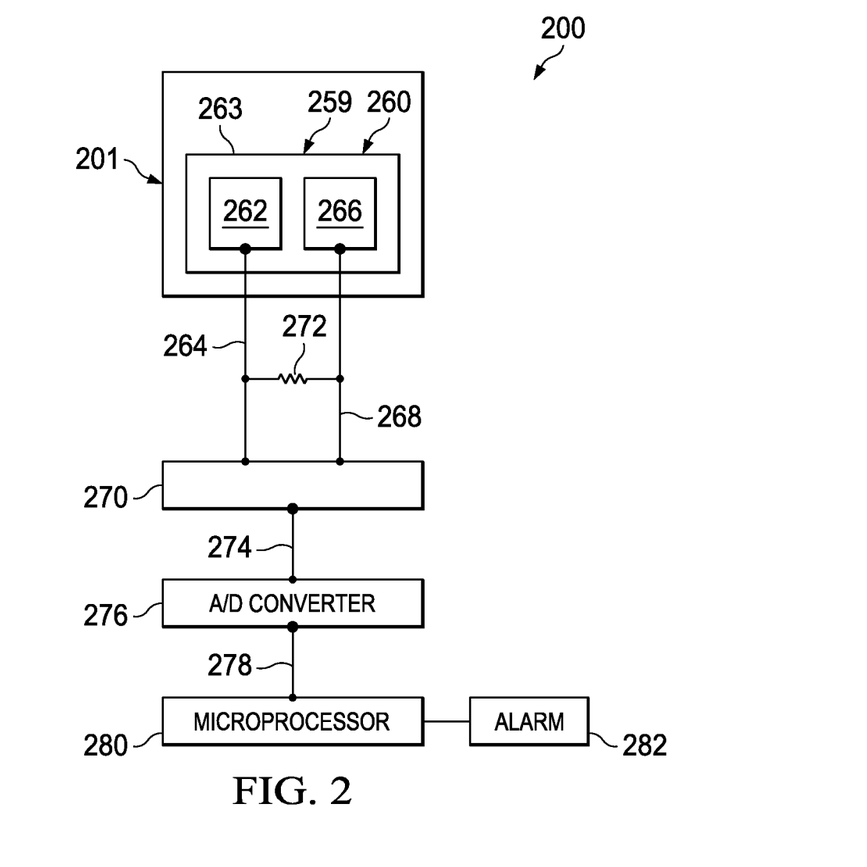
FIG. 2 is a schematic diagram of an illustrative embodiment of galvanic cell on a wound dressing.

A monitoring unit 170 is electrically coupled to the first electrical lead 164 and the second electrical lead 168 and is configured to detect voltage, current, or power generated by the first galvanic cell 160. As shown in FIG. 2, the voltage across 272 could be presented to a differential amplifier, or used in a single ended fashion with one end of 272 grounded and the other end presented to an operational voltage amplifier (OP AMP). The monitoring unit 170 includes a circuit for measuring the power or voltage produced, e.g., a comparator circuit. When the ionic fluid substantially saturates the absorbent layer 115 proximate to the first and second electrodes 162, 166, the ionic fluid functions as a salt bridge between the two electrodes 162, 166 and current is produced. The monitoring unit 170 may include a visual or an audible alarm that signals when a threshold power or current has been reached. The alarm, or dressing full signal, signifies that the dressing 101 is full, and more specifically, that the absorbent layer 115 is full.

In operation, according to one illustrative embodiment, the treatment manifold 108 is deployed proximate to the tissue site 104, e.g., in the wound bed on the wound 102, with a portion near a wound edge 109. The absorbent layer 115 is placed proximate to the treatment manifold 108 (if not already attached) to receive ionic fluids. The first galvanic cell 160 is applied to the absorbent layer 115. The sealing member 111 is placed over the tissue site 104 and the treatment manifold 108 and at least partially against epidermis 103 (or gasket or drape) to form a fluid seal and to form the sealed treatment space 154. If not already installed, the reduced-pressure interface 150 is installed. The reduced-pressure delivery conduit 144 is fluidly coupled to the reduced-pressure interface 150 and the reduced-pressure source 140 whereby reduced pressure may be provided to the treatment manifold 108. The reduced-pressure source 140 may be activated to begin the delivery of reduced pressure to the treatment manifold 108 in the sealed treatment space 154.

The reduced pressure delivered will extract exudates into the treatment manifold 108. The exudates are absorbed, at least in part, from the treatment manifold 108 by the absorbent layer 115 and eventually will substantially saturate the absorbent layer 115. As previously discussed, the saturated absorbent layer 115 functions as a salt bridge and the first galvanic cell 160 provides a current flow that may be detected and used to sound an alarm or produce a signal indicating that the absorbent layer 115 is full.

While the illustrative embodiment of FIG. 1 is shown with reduced pressure applied and with a treatment manifold 108, it should be understood that in other embodiments, the absorbent layer 115 may be placed directly proximate to a tissue site. In addition, a reduced-pressure source may not be used to attract exudates or other ionic fluids, but rather a wicking layer may be used with the absorbent layer 115 to attract fluids. It should also be appreciated that a plurality of galvanic cells may be used to provide progressive feedback on the state of fill of the absorbent layer 115. The plurality of galvanic cells may be located in geometrically significant areas where liquids are expected to collect. The positions could also be chosen to indicate the progress of the liquid through the dressing 101 so that an estimation of remaining capacity may be calculated.

Referring now primarily to FIG. 2, a system 200 for treating a tissue site on a patient is shown. The system 200 includes a dressing 201 and an electronic detection device 259. The electronic detection device 259 may include a first galvanic cell 260. The first galvanic cell 260 includes a first electrode 262 electrically coupled to a first electrical lead 264. The first galvanic cell 260 includes a second electrode 266 electrically coupled to a second electrical lead 268. The first and second electrodes 262, 266 may be coupled to a base 263, or stabilizing platform. A power-using device, e.g., a resistor 272, may be electrically coupled between the first electrical lead 264 and the second electrical lead 268. A voltage may be measured between the electrical leads 264, 268 by a monitoring unit 270. The voltage between the electrodes 262, 266 will rise above a threshold value as the absorbent layer 115 becomes saturated proximate to the electrodes 262, 266. In one illustrative, non-limiting embodiment, the longitudinal length of the base 263 is 20 mm, the width is 10 mm, and the electrodes are 8 mm by 8 mm.

The monitoring unit 270 may produce an analog signal indicative of the voltage and that signal may be delivered by a third lead 274 to an analog-to-digital converter 276. A digital signal may then be delivered by a fourth lead 278 to a microprocessor unit 280. The microprocessor unit 280 may monitor and manipulate the signal as desired. Upon determining that a threshold value has been reached, the microprocessor unit 280 may provide a signal to an alarm 282 (visual or audible) or to another unit.

Figure 3:
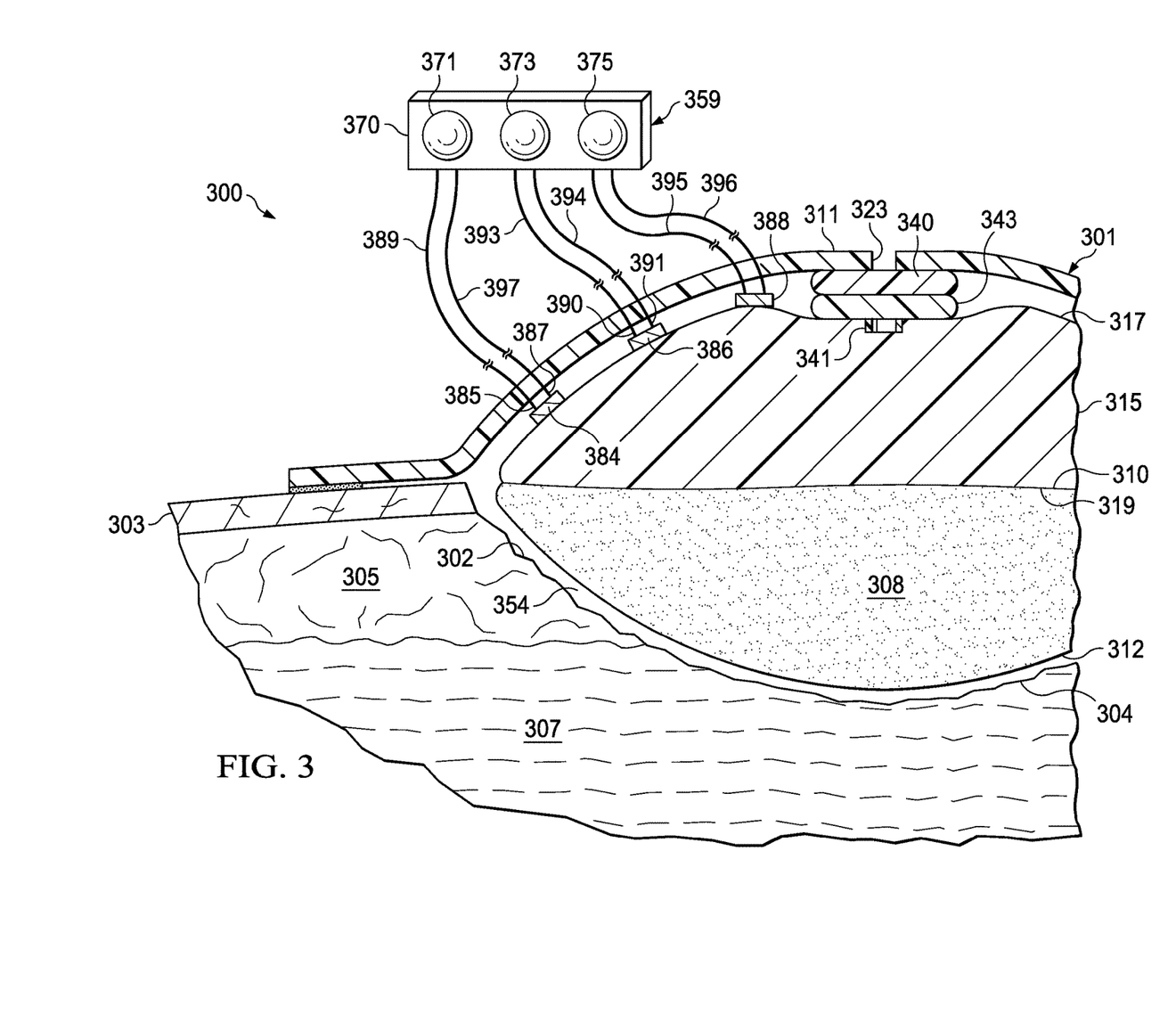
FIG. 3 is a schematic cross section of a portion of an illustrative embodiment of a dressing with a conductive loop.
Figure 4A:
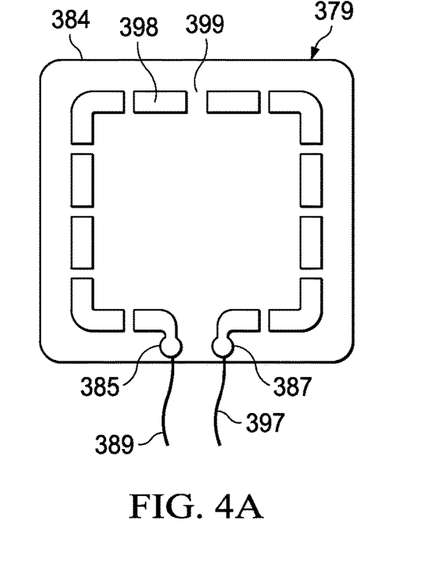
FIG. 4A is a schematic top view of an illustrative embodiment of a conductive loop for use with a dressing, such as the dressing in FIG. 3, showing a plurality of conductive gaps.
Figure 4B:
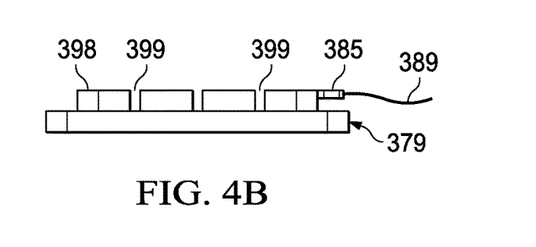
FIG. 4B is a schematic side view of the conductive loop of FIG. 4A.
Figure 5:
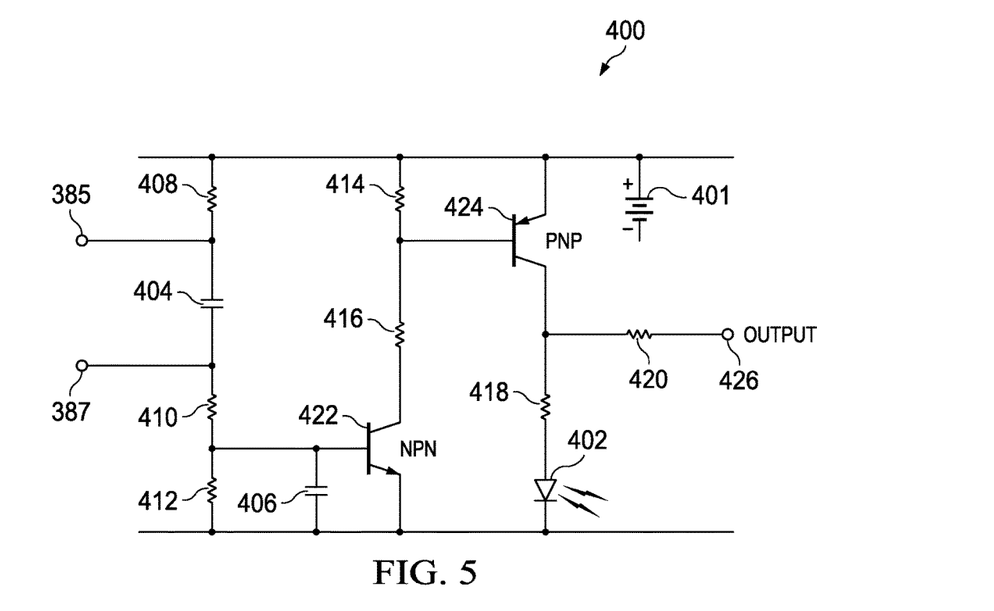
FIG. 5 is a schematic diagram of an illustrative embodiment of a circuit for use with the conductive loop of FIGS. 4A-4B.

Referring now primarily to FIGS. 3-5, another illustrative embodiment of a reduced-pressure system 300 and dressing 301 is presented. The reduced-pressure system 300 includes an electronic detection device 359. The electronic detection device 359 may include one or more conductive loops, e.g., a first conductive loop 384, a second conductive loop 386, and a third conductive loop 388. It should be understood that the "conductive loops" are selectively conductive or only conductive at times when the circuit is completed as is described herein. Similar to the previously presented embodiments, the dressing 301 may include a treatment manifold 308 having a first side 310 and a second side 312. The dressing 301 includes an absorbent layer 315, which has a first side 317 and a second, patient-facing side 319. In another illustrative embodiment, the system 300 excludes the treatment manifold 308, and the second, patient-facing side 319 of the absorbent layer 315 is placed adjacent to the tissue site 304.

In the illustrative embodiment shown, the treatment manifold 308 is placed proximate to the tissue site 304. The tissue site is a wound 302 that extends through epidermis 303, through dermis 305 and into subcutaneous tissue 307. A sealing member 311 is placed over the absorbent layer 315 and optionally (if included) over the treatment manifold 308 to form a sealed space 354. Thus, the conductive loops 384, 386, 388 are disposed under the sealing member 311 and proximate to the absorbent layer 315. The conductive loops 384, 386, 388 are in the sealed space 354.

A reduced-pressure source 340 is covered by the sealing member 311 and provides reduced pressure in the sealed space 354. The sealing member 311 includes an aperture 323 to allow the reduced-pressure source 340 to vent. The reduced-pressure source 340 may be a micro pump, a diaphragm pump, disc pump, piezoelectric pump, or other small pump. In the illustrative embodiment, the reduced-pressure source is built into the dressing 301. A layer 343 may be included to help distribute reduced pressure or prevent fluids from entering the reduced-pressure source 340. It should be understood that other sources of reduced pressure may be utilized and in other embodiments may be excluded altogether. The reduced-pressure source 340 may utilize a connecting member 341 to fluidly couple the reduced-pressure source 340 to the absorbent layer 315. In another embodiment, the connecting member 341 may extend through the absorbent layer 315 and directly couple the reduced-pressure source 340 to the treatment manifold 308.

According to an illustrative embodiment, in operation, as before, the dressing 301 receives exudates or other ionic fluid from the tissue site 304 and stores the exudate in the absorbent layer 315. The absorbent layer 315 may have a wicking layer to help pull exudate from the treatment manifold 308. When the absorbent layer 315 becomes fully saturated, the absorbent layer 315 will no longer hold additional exudate. Accordingly, the patient or healthcare provider will want to be alerted when the absorbent layer 315 is saturated. The conductive loops 384, 386, 388 (with speaker or visual alert or the another alert device) provide such an alert.

The plurality of conductive loops 384, 386, and 388 are added to the absorbent layer 315 to help provide an indication of the fullness of the absorbent layer 315. The first conductive loop 384 includes a first terminal 385 and a second terminal 387. The first terminal 385 is coupled by a first electrical lead 389 to a monitoring unit 370 that includes a first LED 371, a second LED 373, and a third LED 375. The second terminal 387 is coupled by a second electrical lead 397 to the monitoring unit 370.

The monitoring unit 370 includes circuitry that provides power to the conductive loops 384, 386, and 388. The conductive loops 384, 386, 388 contain conductive gaps 399 that are electrically bridged when sufficient exudate reaches the conductive loops 384, 386, 388. Sufficient exudate reaches the conductive loops at least when liquid saturates the absorbent layer 315 in the area of the conductive loop involved as will be explained further below. The second conductive loop 386 has a first terminal 390 and a second terminal 391. The first terminal 390 and the second terminal 391 of the second conductive loop 386 are electrically coupled by leads 393 and 394 to the monitoring unit 370 and are particularly associated with second LED 373. Similarly, the third conductive loop 388 includes leads 395 and 396 that are electrically coupled to the monitoring unit 370 and are associated with third LED 375.

FIGS. 4A and 4B show the first conductive loop 384, which is representative of the other conductive loops 386, 388. The first conductive loop 384 contains a conductive path 398 formed with one or more conductive gaps 399. The conductive path 398 may be mounted on a base 379. To help safeguard against premature signaling, an electrical insulation layer (not explicitly shown) may cover the conductive path 398 and have apertures only at the conductive gaps 399. It will be appreciated that as an ionic fluid surrounds and covers the conductive path 398, the ionic fluid will electrically couple the conductive gaps 399. In other words, the ionic fluid serves as an electrical bridge for the conductive gap 399 and allows the conductive path 398 to carry a current. When the current is carried sufficiently, the monitoring unit 370 provides a signal, such as first LED 371. The other conductive loops 386, 388 are analogous. It should be understood that while three conductive loops 384, 386, and 388 are shown, any number of conductive loops may be used. Multiple conductive loops may be used to assess saturation of the dressing 301 at different locations and provide an escalating scale of fullness for the dressing 301.

Referring now primarily to FIG. 5, an illustrative embodiment of a detection circuit 400 is presented. Numerous circuit designs may be used and detection circuit 400 is only an illustrative embodiment of one. The detection circuit 400 may be included in the monitoring unit 370. The detection unit 400 may be configured to power an LED 402 in response to a current flowing through the first terminal 385 and the second terminal 387 indicating exudate in the dressing 301 as sensed by a completed conduction or conductive path. The detection circuit 400 may, for example, provide a conductive loop that supplies a voltage from a battery 401 to the LED 402 in response to activation by a small current passing between the first terminal 385 and the second terminal 387.

The detection circuit 400 may utilize at least two capacitors 404 and 406 to respond to the current through the first terminal 385 and the second terminal 387. A number of resistors 408, 410, 412, 414, 416, 418, and 420 in the detection circuit 400 generate voltage differentials that function with the capacitors 404 and 406 to drive a NPN transistor 422 and a PNP transistor 424 to activate the LED 402.

A completed conductive path across the first terminal 385 and second terminal 387 allows current through the resistor 408 to bypass the capacitor 404. Current flows through the resistor 410 to the base of the NPN transistor 422, rather than through the higher resistance path provided by resistor 412. The current entering the base of the NPN transistor 422 amplifies the current allowed to flow into the NPN transistor 422 through the resistors 414 and 416. The NPN transistor 422 is "on" when the base is pulled high by the input signal through the resistor 410 relative to the emitter output.

The PNP transistor 424 is "on" when the base receiving current through the resistor 414 is pulled low relative to the emitter. As a result, the current through the base of the NPN transistor 422 activates the PNP transistor 424 to amplify current to the collector supplying current to the resistor 418 and the LED 402. As a result, the NPN transistor 422 and the PNP transistor 424 are only activated to supply a current lighting the LED 402 in response to the first terminal 385 and the second terminal 387 completing a closed circuit or conductive path.

The detection circuit 400 may also include an output 426 that functions as a terminal. The output 426 may communicate a signal received through the resistor 420 indicating that the PNP transistor 424 has been activated thereby supplying current through the LED 402. The output 426 may communicate with a recording or logging device that records the point at which the conduction path was created between the first terminal 385 and the second terminal 387. This information or data may be utilized to track the presence of a threshold level of exudate in the dressing 301.

When the exudate within the dressing is insufficient to complete the conduction path between terminals 385 and 387, the detection circuit 400 is inactive. The DC current passing through the resistor 408 from the battery 401 is blocked by the capacitor 404. As a result, neither the NPN transistor 422 nor the PNP transistor 424 is activated to supply current to the LED 402.

In other embodiments, the detection circuit 400 may be replaced by other current detection circuits. The resistance, capacitance, and other characteristics of the detection circuit 400 may vary based on the sensitivity of the readings across the first terminal 385 and the second terminal 387 and the power requirements of the LED 402. In another illustrative embodiment, the LED 402 may be replaced by a visual or digital indicator that, based on the level of current passing through the resistor 418 to the indicator, indicates the amount or type of exudate within the dressing 301. The indicator may be an analog or digital element specifically calibrated to provide audible, visual, or tactile feedback to one or more users.

According to another illustrative embodiment, a capacitive sensor may be located on an exterior of the dressing, e.g., on the sealing member 111 above where electrode 162 is shown in FIG. 1. The capacitive sensor has a sensing profile that measures capacitance at a location that fills last. When liquids reach the location that corresponds with the sensing profile, the capacitance of the portion of the dressing associated with the capacitive sensor changes within the dressing as seen by the fill sensor. As a result, the capacitance sensor produces a signal indicating that the dressing is saturated.

According to another illustrative embodiment, a dye is placed in the absorbent layer, e.g., absorbent layer 315, that provides a change visual appearance (or optical properties) upon becoming wet. The visual indication may be a change in contrast, change in color, change in brightness, a change in reflectivity or other visual cue. The change in visual appearance may be a change perceptible to a human eye or only to a device, e.g., an electrical photo detector. The electrical photo detector may detect more subtle changes in visual appearance. The electrical photo detector is attached proximate to the sealing member 311 and can optically detect the change in contrast and produce a signal indicative of the change. Thus, as the absorbent layer 315 becomes saturated, the dye changes contrast, the optical detector senses the change in contrast, and develops a full signal. In another embodiment, the dye may be placed in the treatment manifold, e.g., manifold 108.

According to still another illustrative embodiment, metal capacitance plates are put within or near the absorbent layer, e.g., absorbent layer 315, having defined space between plates. The capacitance changes as the ionic fluid fills the space between the plates. The change in capacitance is measured and the change is noted when the ionic fluid fills the space between the plates.

Figure 6:
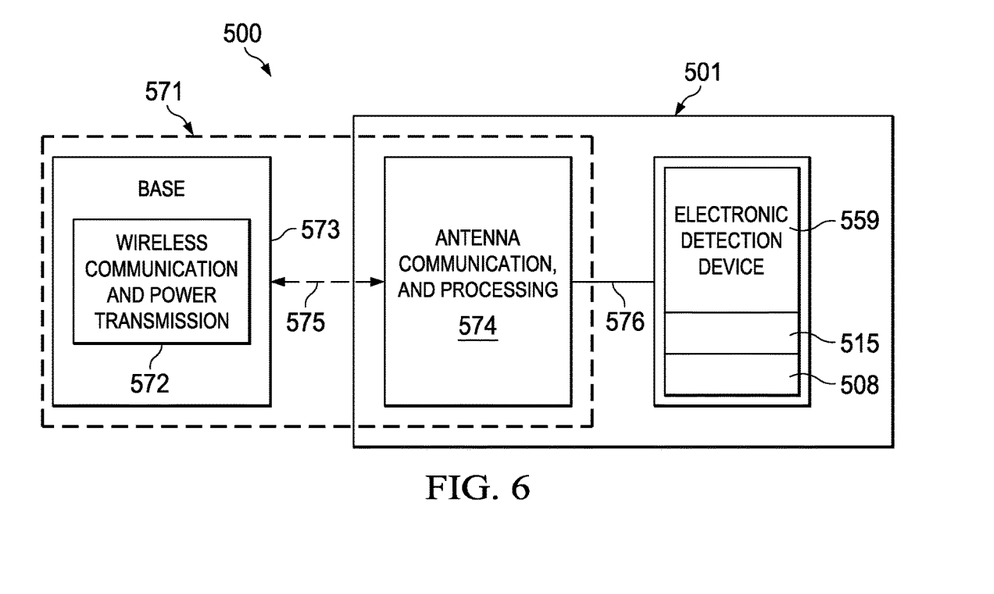
FIG. 6 is a schematic diagram of an illustrative embodiment of a reduced-pressure treatment system that includes a wireless-communication-and-power subsystem.

Referring now primarily to FIG. 6, a schematic diagram of another illustrative embodiment of a reduced-pressure treatment system 500 is presented. The reduced-pressure treatment system 500 includes a wound dressing 501 that may include a manifold 508 and an absorbent layer 515. An electronic detection device 559 is associated with the absorbent layer 515 and is configured to electronically determine when the absorbent layer (or some portion thereof) is substantially saturated. The electronic detection device 559 may be, for example, a galvanic cell or a conductive loop with conductive gaps or other means of electronically determining when the absorbent layer 515 is substantially saturated.

Associated with the electronic detection device 559 is a wireless-communication-and-power subsystem 571. The wireless-communication-and-power subsystem 571 may provide power to the electronic detection device 559 and may wirelessly receive information related to the status of the absorbent layer 515 as produced by the electronic detection device 559. The wireless-communication-and-power subsystem 571 may include a wireless-communication-and-power-transmission unit 572, which is on a base station 573, and an antenna-communication-and-processing unit 574. The wireless-communication-and-power subsystem 571 is analogous to a Radio-Frequency Identification Device (RFID). Power is transmitted by a wireless signal 575 from the wireless-communication-and-power-transmission unit 572 to the antenna-communication-and-processing unit 574 from where the power is provided by coupling 576 to the electronic detection device 559.

The power provided to the electronic detection device 559 may augment power already developed, e.g., by a galvanic cell, or provide all the power, e.g., for a resistive circuit. In any event, the electronic detection device 559 is configured to determine if the absorbent layer 515 is saturated or possibly to what extent liquid exists within the absorbent layer 515 and to produce a signal with the relevant information. The signal may be delivered by coupling 576 to the antenna-communication-and-processing unit 574 from where a wireless signal 575 carries the information to the wireless-communication-and-power-transmission unit 572. The wireless-communication-and-power-transmission unit 572 may further process the signal for display or use by other systems monitoring or controlling the reduced-pressure treatment system 500. As such, with this embodiment, no direct electronic connection is required between a monitoring device and the electronic detection device 559. Accordingly, less power may be needed and comfort may be enhanced.

The systems 100, 200, 300, 500 presented, allow for the saturation of the absorbent layer, e.g., 115, 215, 315, 515 to be determined using an electrical device. Because a visual determination or a tactile inspection is not required, the electrical signal may be used to set off an alarm or otherwise signal the user or healthcare provider that the dressing is saturated and should be changed. Moreover, by arranging the components, intermediate indications of the percentage full may be provided. It should be understood that the output signal also enables easy interface with an electronic controller or circuit in an analog or digital system.

In another illustrative embodiment, the systems and methods for receiving an ionic fluid may be analogous to the systems and methods previously presented, but the system may not utilize an absorbent layer, e.g., absorbent layer 115 in the reduced-pressure treatment system 100 may be omitted. In such an embodiment, the electrodes are fluidly coupled to a portion of a dressing that will be exposed to liquids last as the liquids build up in the dressing. In still another embodiment, the dressings of FIGS. 1-4B, may be used without reduced pressure, but may use wicking from the absorbent layer and may include additional wicking layers. In this embodiment, a completed circuit would indicate saturation of the dressing and signal a needed change.

Although the present invention and its advantages have been disclosed in the context of certain illustrative embodiments, it should be understood that various changes, substitutions, permutations, and alterations can be made without departing from the scope of the invention as defined by the appended claims.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems. For example, each of the sensor types (galvanic sensors, conductive sensors, capacitive sensors) may be utilized with each of the pump types (external to the dressing, internal to the dressing, or without any pump). The various sensor types may be used in any number of combination of types as required.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A dressing for receiving an ionic fluid, the dressing comprising:
   a treatment manifold adapted to be disposed adjacent a tissue site;
   an absorbent layer for disposing over the treatment manifold, placing in fluid communication with a tissue site, and receiving and at least temporarily retaining ionic fluids from the tissue site, the absorbent layer having a first side and a second, patient-facing side;
   a sealing member for covering the absorbent layer and the treatment manifold;
   a reduced-pressure interface having an elbow port, the reduced-pressure interface adapted to be coupled to the sealing member, and the elbow port adapted to extend through the absorbent layer to be fluidly coupled to the treatment manifold;
   a plurality of galvanic cells associated with the absorbent layer and configured to provide power proportional to the saturation of the absorbent layer of the dressing; and
   a first galvanic cell of the plurality of galvanic cells located at a position on the absorbent layer and configured to produce a voltage above a threshold voltage to indicate when the absorbent layer proximate to the first galvanic cell is substantially saturated with the ionic fluid.

2. The dressing of claim 1, wherein each galvanic cell of the plurality of galvanic cells comprises:
   a first electrode and a second electrode, the first electrode and the second electrode in fluid communication with a portion of the absorbent layer, and the first electrode and the second electrode spaced from one another;
   a first electrical lead coupled to the first electrode;
   a second electrical lead coupled to the second electrode; and
   wherein the first electrode and the second electrode are configured to produce measurable electrical power when the ionic fluid covers the first electrode and the second electrode.

3. The dressing of claim 2, wherein the first electrode comprises copper and the second electrode comprises tin.

4. The dressing of claim 2, wherein the first electrode comprises copper and the second electrode comprises tin, and wherein the ionic fluid comprises exudate from a patient.

5. The dressing of claim 2, wherein the first electrode comprises copper and the second electrode comprises zinc.

6. The dressing of claim 1, further comprising a wireless-communication-and-power subsystem.

* * * * *